(12) United States Patent
Lewis

(10) Patent No.: US 8,096,975 B2
(45) Date of Patent: Jan. 17, 2012

(54) INJECTOR AND THERMAL JACKET FOR USE WITH SAME

(76) Inventor: Van L. Lewis, Roanoke, VA (US)

(*) Notice: Subject to any disclaimer, the term of this patent is extended or adjusted under 35 U.S.C. 154(b) by 663 days.

(21) Appl. No.: 12/153,968

(22) Filed: May 28, 2008

(65) Prior Publication Data

US 2008/0300540 A1 Dec. 4, 2008

Related U.S. Application Data (60) Provisional application No. 60/924,713, filed on May 29, 2007.

(51) Int. Cl.
*A61F 7/12* (2006.01)
(52) U.S. Cl. ............................................ 604/113
(58) Field of Classification Search ............ 604/113; 417/153; 606/92, 93, 208
See application file for complete search history.

(56) References Cited

U.S. PATENT DOCUMENTS

| | | | | |
|---|---|---|---|---|
| 2,687,626 A * | 8/1954 | Bartlowe | ............ | 62/276 |
| 4,038,519 A * | 7/1977 | Foucras | ............ | 392/472 |
| 4,214,147 A * | 7/1980 | Kraver | ............ | 392/468 |
| 4,801,263 A | 1/1989 | Clark | | |
| 5,211,631 A * | 5/1993 | Sheaff | ............ | 604/113 |
| 5,601,894 A * | 2/1997 | Maruschak | ............ | 428/36.9 |
| 6,432,344 B1 * | 8/2002 | Eckman et al. | ............ | 264/263 |
| 6,613,069 B2 * | 9/2003 | Boyd et al. | ............ | 606/205 |
| 6,746,439 B2 * | 6/2004 | Lenker | ............ | 604/500 |
| 6,793,660 B2 | 9/2004 | Kerr et al. | | |
| 7,357,789 B2 * | 4/2008 | Bills | ............ | 604/187 |
| 7,711,251 B2 * | 5/2010 | Barkey | ............ | 392/468 |
| 7,837,678 B2 * | 11/2010 | Thompson et al. | ............ | 606/32 |
| 2004/0199115 A1 * | 10/2004 | Rosenman | ............ | 604/113 |
| 2006/0271014 A1 | 11/2006 | Hynes et al. | | |
| 2007/0142773 A1 * | 6/2007 | Rosiello et al. | ............ | 604/113 |
| 2008/0177231 A1 * | 7/2008 | Saab | ............ | 604/113 |
| 2008/0188808 A1 * | 8/2008 | Hynes et al. | ............ | 604/113 |

* cited by examiner

*Primary Examiner* — Jackie Ho
*Assistant Examiner* — Diva Ranade
(74) *Attorney, Agent, or Firm* — Kelley Drye & Warren, LLP (57) ABSTRACT

An apparatus for injecting a material comprising an injector barrel in communication with a delivery needle and a plunger, wherein at least a portion of the plunger is slidably disposed within a proximal portion of the injector barrel, and a proximal end of the delivery needle is in communication with a distal end of the injector barrel, and a thermal jacket surrounding at least a portion of the length of the injector barrel is disclosed. The thermal jacket may be used to regulate the temperature of the material to be delivered.

17 Claims, 7 Drawing Sheets

END VIEWS

INJECTOR AND THERMAL JACKET FOR USE WITH SAME

CROSS REFERENCE TO RELATED APPLICATIONS

The present invention relates to, and is entitled to the benefit of the earlier filing date and priority of, Application No. 60/924,713, filed on May 29, 2007, which is herein incorporated by reference as if fully set forth.

FIELD OF INVENTION

The apparatus according to an embodiment of the present invention is an injector comprising a thermal jacket. More particularly, the apparatus and method of using the apparatus improves control of the injection of bone cement for medical procedures by the use of 1) mechanical (high pressure/low compliance) and 2) thermal elements.

BACKGROUND

In the industry, variability of cement reaction temperature results in variability in injection and delivery characteristics. Many low compliance injectors like the 1 cc syringe and other commercially available injectors may increase radiation exposure to the operator.

Bone cement temperature can vary considerably and therefore its handling characteristics can vary. Currently available injectors may have low compliance but forces operator to remain close to the radiation source, for example an x-ray beam, wherein other injectors have lesser compliance but allow further distance from the x-ray beam.

Others have attempted to solve the problem by using water baths to adjust the temperature of the cement, freezing the cement in the injector, adjusting the temperature of the orthopedic appliances being placed at surgery, adjusting the cement polymerization time by changing its components, and constructing the injector out of low-compliance materials. All of these attempts have failed to solve the current problems.

U.S. Pat. No. 6,264,659 to Ross et al. describes the use of heat only with no possibility or need for cooling. In Ross et al. the reaction is a phase change in the thermoplastic material rather than a polymerization reaction which changes the chemicals irreversibly. Applicant uses thermal elements to control the rate of a chemical reaction. In Ross et al. there is no need for the operator of the device to be a certain distance from the patient (no radiation), as distance from the patient is not an issue, it is better for the operator to be closer to the patient so that the material does not set before entering the disc.

U.S. Pat. No. 5,324,305 to Kanner describes the use of a thermoplastic heater with a solid bio adhesive which flows when heated, and is used to treat the eyes. The bio adhesive is a solid at room temperature, and must be "melted" for application and operates like a glue gun.

U.S. Publication No. 2005/0245938 to Kochan describes a detachable balloon filled with the thermoplastic material in addition to heating a thermoplastic elastomer to treat intervertebral discs or articular joint spaces.

U.S. Publication No. 2006/0122625 to Truckai et al. describes changing the temperature of the bone cement by radiofrequency energy generated heat, and in some embodiments not confined to the tip of the probe but also occurring within the tissue. Truckai et al. also alludes to using other energy forms to heat the cement, such as laser, ultrasound, etc., but does not disclose cooling or heating or using other chemical agents to create hot or cool temperatures. Truckai et al. focuses primarily on heating to accelerate the cement polymerization process. Applicant uses cooling and heating together serially or individually to speed or slow the reaction of the cement.

In addition to the above, greater control of cement delivery through mechanical (elongated small barrel syringe) and/or thermal jacket, control of polymerization, and increased radiation safety by maintaining distance from the x-ray beam is needed in the industry.

Advantages of some embodiments of the present invention may include, in part, but are not limited to, less compliance of injector; 1:1 control when pushing or pulling on syringe; reduced movement of connecting and unconnecting syringe to needle; total volume for each injection is in its own syringe; two syringes for two needle procedure, reduced radiation exposure for operator and patient, altering the working time and viscosity of the bone cement by altering the temperature of the thermal jacket, use with different cement formulations which inherently set up faster or slower; and accelerating or slowing the cement polymerization reaction, and use of two injectors for two needle procedures facilitating delivery and use of radiation shields. Commonly this would be useful in treating spinal fractures, as with vertebroplasty or kyphoplasty.

SUMMARY

Responsive to the foregoing challenges, Applicant has developed an innovative device for controlling the temperature of a material before introduction to a patient. An embodiment of the present invention is an apparatus for injecting a material comprising an injector barrel in communication with a delivery needle and a plunger, wherein at least a portion of the plunger is slidably disposed within a proximal portion of the injector barrel, and a proximal end of the delivery needle is in communication with a distal end of the injector barrel, and a thermal jacket surrounding at least a portion of the length of the injector barrel. The apparatus may also include an introducer cannula and the injector barrel may incorporate a flexible distal segment near the distal end of the injector barrel. The distal portion of the plunger may be flexible. An advancement mechanism may be in communication with the plunger. The thermal jacket may comprise an interior wall, an exterior wall, and first and second end walls connected to the interior and exterior walls creating a closed tubular system enclosing a thermal space. A heating element may be disposed on the injector barrel. The thermal jacket may comprise a port disposed on the exterior wall and in communication with the thermal space. An embodiment of the present invention is an apparatus for injecting a material, comprising an injector barrel with a proximal and a distal end, wherein the distal end is in communication with a delivery handle, a plunger with a proximal end and a distal end, wherein a portion of the distal end is in communication with the proximal end of the injector barrel, wherein at least a portion of the plunger is slidably disposed within the injector barrel, and a thermal jacket surrounding at least a portion of the length of the injector barrel, wherein the thermal jacket comprises an interior wall and exterior wall joined by a first end wall and a second end wall. The thermal jacket may comprise at least two chambers with a partition to isolate the two chambers from one another. A heating element may be disposed at the distal end of the thermal jacket. The thermal jacket may have an opening along its length. The thermal jacket may have a hinge disposed on the external wall opposite the opening. An embodiment of the present invention is an apparatus for injecting a material comprising, an injector barrel, a plunger, a thermal jacket, wherein the thermal jacket contains both a cooling portion and a heating portion. The cooling portion may be cooled by the circulation of a cold liquid in the thermal jacket. The heating portion may be disposed on the injector barrel or on the thermal jacket and may be an electric coil.

It is to be understood that both the foregoing general description and the following detailed description are exemplary and explanatory only, and are not restrictive of the invention as claimed. The accompanying drawings, which are incorporated herein by reference, and which constitute a part of this specification, illustrate certain embodiments of the invention and, together with the detailed description, serve to explain the principles of the present invention.

BRIEF DESCRIPTION OF THE DRAWINGS

In order to assist in the understanding of this invention, reference will now be made to the appended drawings, in which like reference characters refer to like elements.

DETAILED DESCRIPTION

Reference will now be made in detail to embodiments of the present invention, examples of which are illustrated in the accompanying drawings. As embodied herein, the present invention is an injector and a thermal jacket, one embodiment of which is an injector and thermal jacket for use during a surgical procedure.

Figure 1:
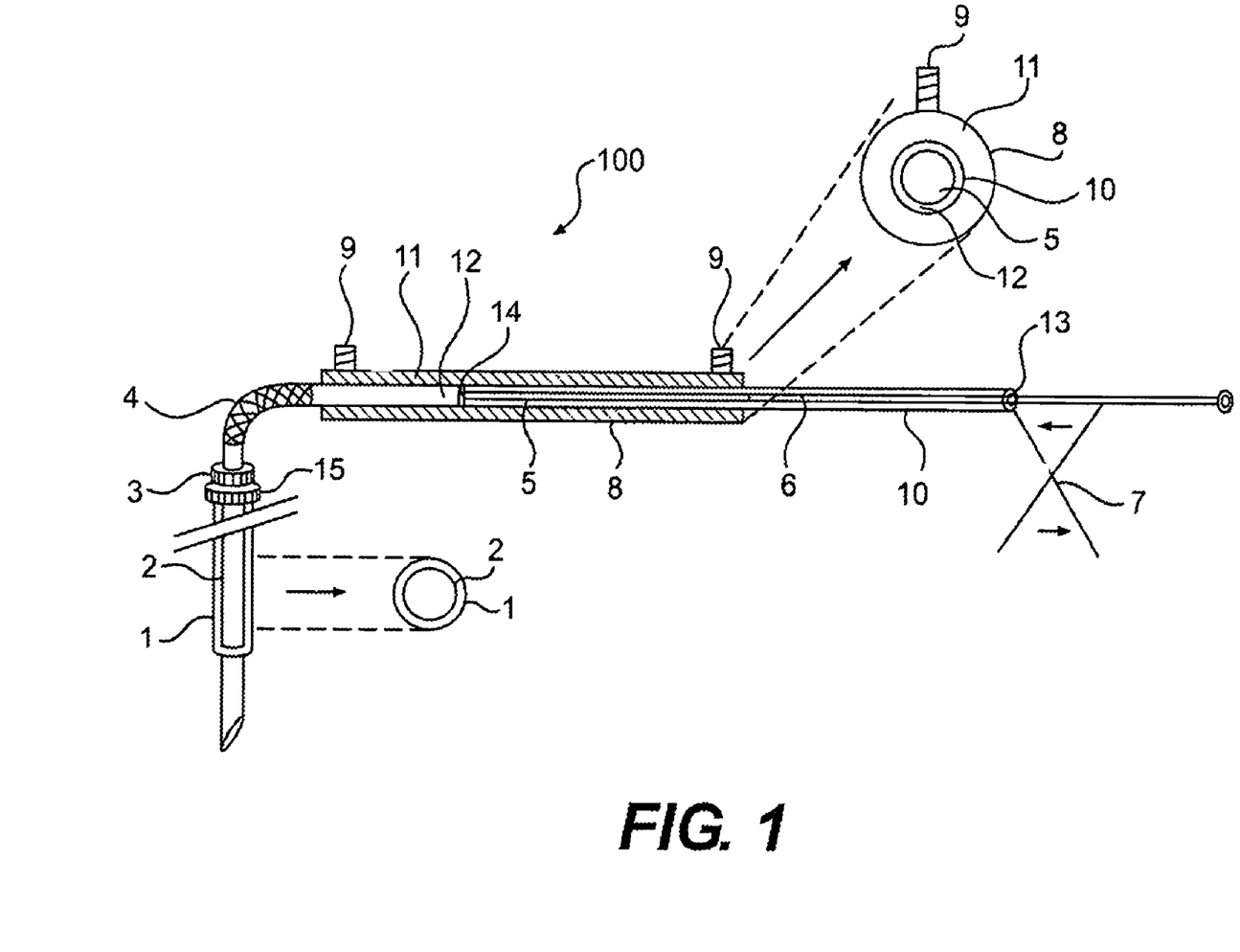
FIG. 1 is a cross-section of a delivery apparatus according to an embodiment of the present invention.
Figures 2A, 2B, 2C:
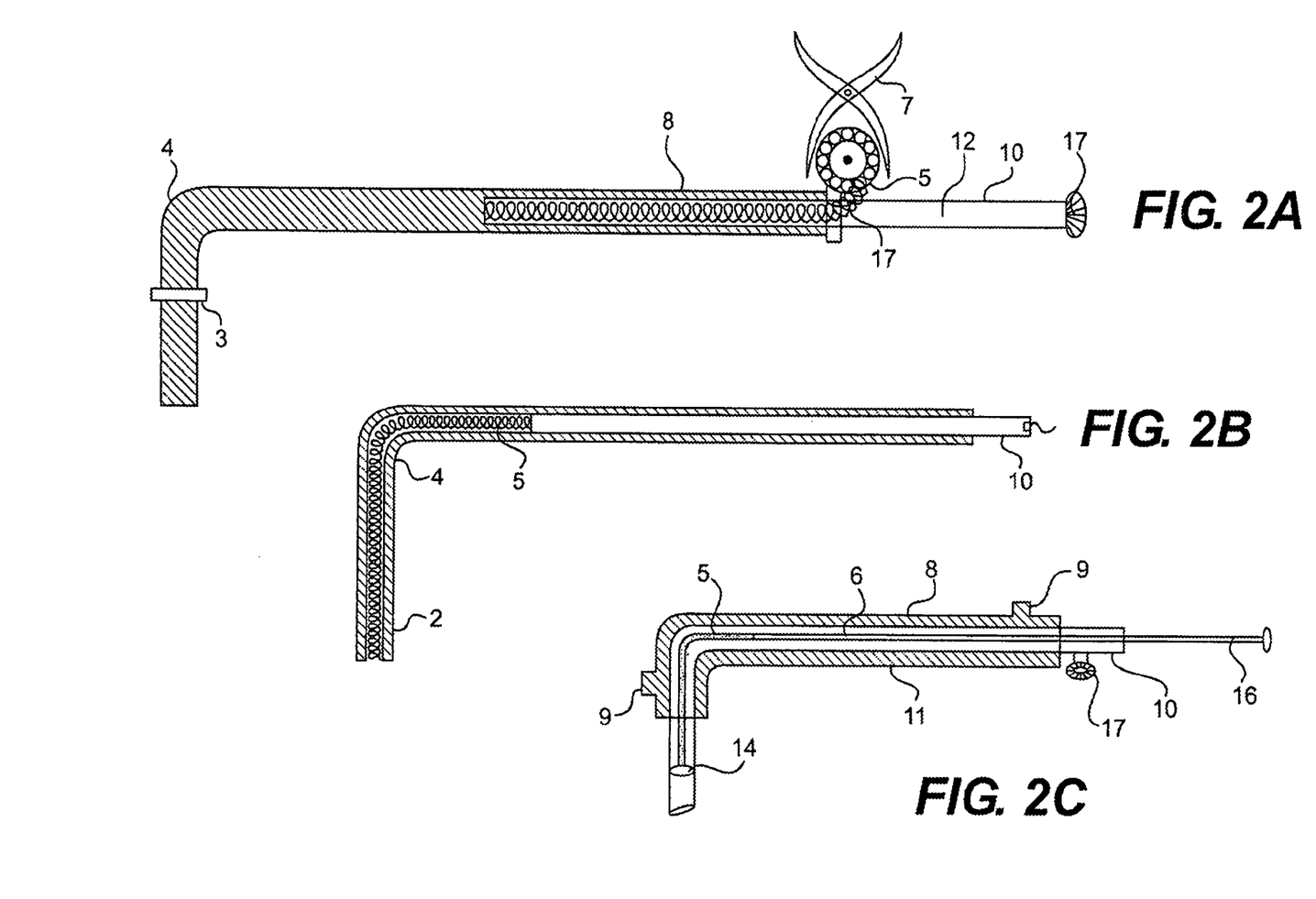
FIG. 2 is a cross-section of an embodiment of the present invention including a flexible plunger.
Figures 3A, 3B:
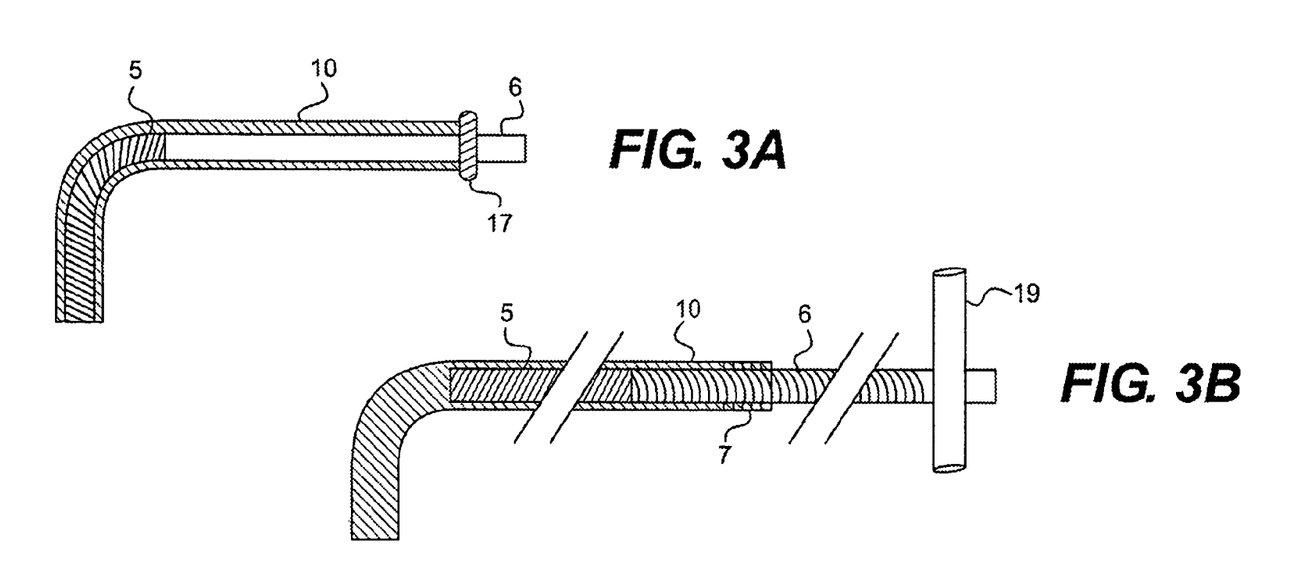
FIG. 3 is a cross-section of an embodiment of the present invention including a threaded plunger and barrel.
Figure 3C:
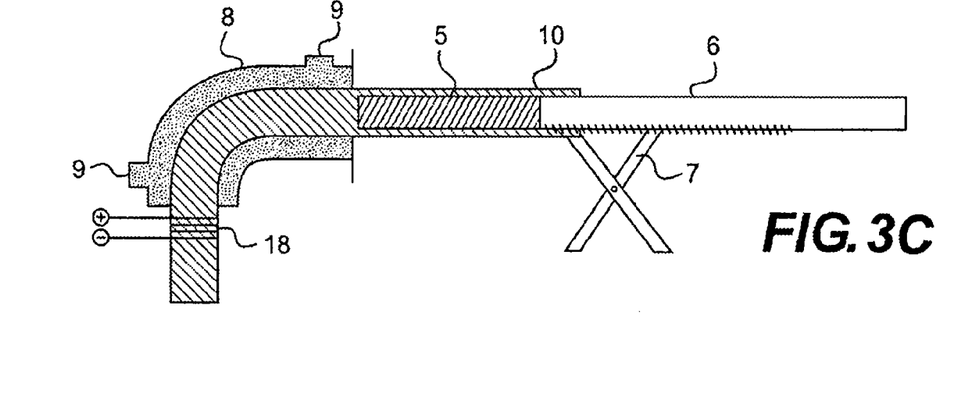

An embodiment of the present invention is shown in FIG. 1 as bone cement delivery apparatus 100. As shown in FIGS. 1, 2, and 3, bone cement delivery apparatus 100 comprises injector barrel 10, cement delivery needle 2, plunger 5, and thermal jacket 8. Optionally, introducer cannula 1 is placed into the patient, usually percutaneously, to the cement delivery site. Cement delivery needle 2 is sized to fit within and a portion to be slidably disposed within the lumen of cannula 1. Cannula 1 may be optional if injector barrel 10 is attached directly to needle 2 which is passed through the skin and, for example, into the bone of the patient.

Cement delivery channel 12 is a lumen in communication with needle 2, flexible or bent distal segment 4 and proximal end 13 of injector barrel 10. Needle 2 may be inserted through cannula 1 and to the delivery site for cement delivery. Needle 2 may be a separate element connected to the distal end of distal segment 4 at connector 3, which may be a Luer-lock type connector, or needle 2 and distal segment 4 of barrel 10 may be one continuous piece, as shown in FIG. 2B.

Luer-lock type connector 3 may also include an attachment connector 15, for example another Luer-lock type connector, to connect needle 2 to cannula 1 after introduction into the patient to help prevent movement of needle 2 within cannula 1 during injection of the cement.

Distal segment 4 of barrel 10 may be comprised of a flexible material, or a material bent to a pre-determined angle, to allow distal segment 4 to bend relative to barrel 10. If flexible, the flexible portion may be comprised of a non-compliant material to help reduce changes in the internal and/or external diameter of segment 4 during delivery of the cement.

Plunger 5 may be flexible or rigid, or in an embodiment, plunger 5 may have a distal flexible portion in communication with a proximal rigid portion 6. Proximal is defined herein as an end or portion closest to the operator, wherein distal is the end or portion away from the operator. Plunger 5 is sized such that it is movably disposed within barrel 10. In one embodiment, the distal end of plunger 5 is sized to enable a snug fit against the inner wall of barrel 10, to allow movement of plunger 5 within barrel 10, but to minimize leakage of cement between the distal end of plunger 5 and inner wall of barrel 10. This may, but not necessarily, be accomplished by the use of optional tip 14 attached to, or incorporated in or near the distal end of plunger 5. Tip 14 may be comprised of an o-ring, or a rubber tip, or any other suitable tip. Snug fit should allow for moving cement forward without significant leak of cement back along plunger 5, but not snug enough to significantly impede movement of plunger 5 through barrel 10. Plunger 5 may be made of metal, plastic, a combination of both, or any other suitable material. In one embodiment the distal portion of plunger 5 is flexible and the proximal portion 6 is rigid, allowing the distal portion of plunger 5 to pass through the bend of distal segment 4 of barrel 10, and on into needle 2, if necessary. In one embodiment distal portion of plunger 5 and proximal portion 6 may be one rigid plunger which then stops at and before entering the bent portion of distal segment 4. Plunger 5 may enter barrel 10 at proximal end 13 of barrel 10, or at port 17 disposed in barrel 10. Port 17 is preferably disposed proximal to thermal jacket 8.

Figure 4:
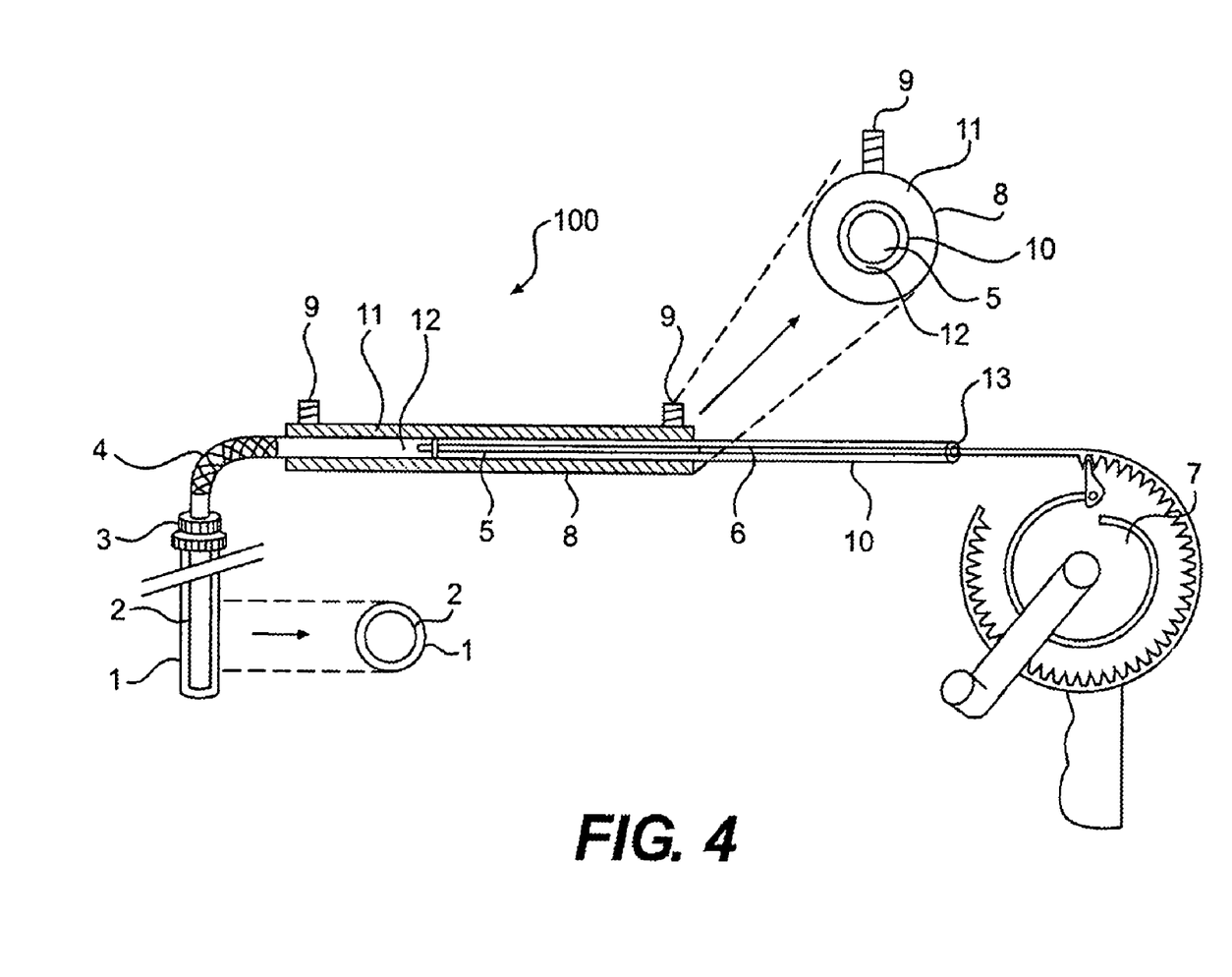
FIG. 4 is a cross-section of an embodiment of the present invention including a ratchet advance mechanism.
Figure 6:
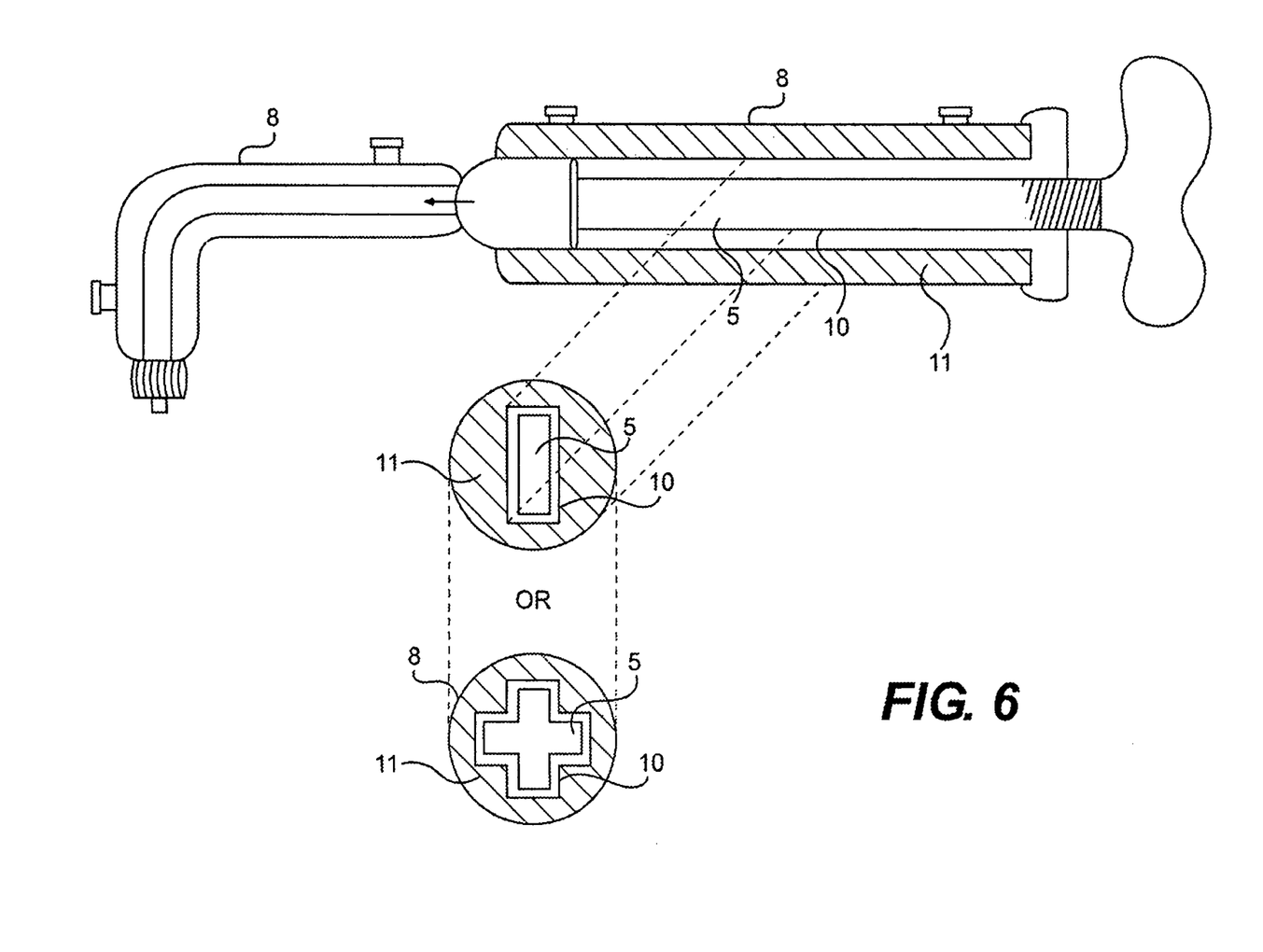
FIG. 6 is a cross-section of one embodiment an embodiment of the present invention including two thermal jackets.
Figure 7:
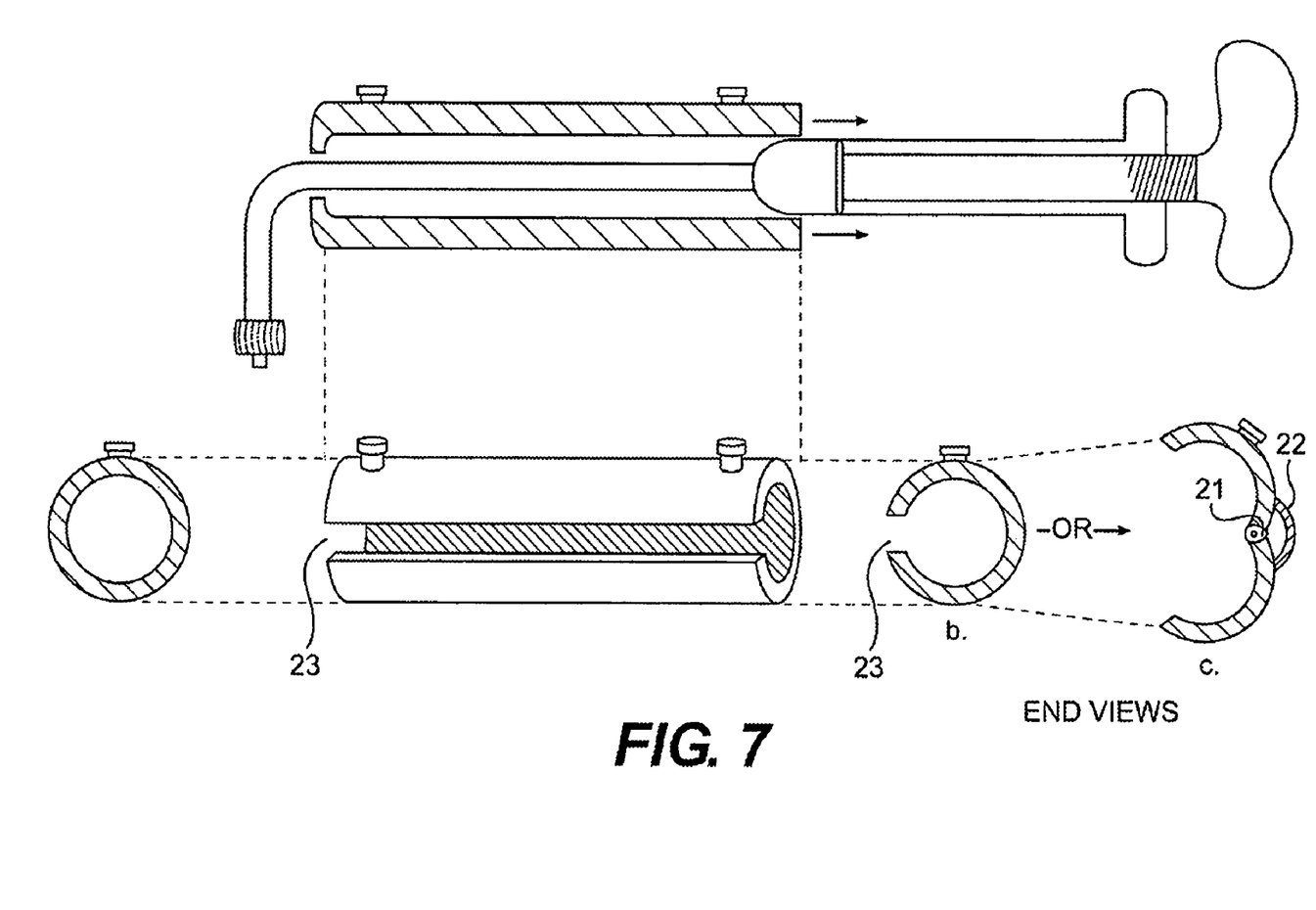
FIG. 7 is cross-section and perspective views of an embodiment of the present invention.

Advancement mechanism 7 as shown in FIGS. 1-4 is a mechanism for advancing and in some embodiments retracting plunger 5 within barrel 10. Advancement may be by hand, by applying pressure to proximal end 16 of plunger 5, or may be by any other suitable mechanical, electrical, or pressurized system. In one embodiment, advancement mechanism 7 may comprise screw-type threads on plunger 5, or on plunger 5 and barrel 10, that engage and permit the operator to advance or retract plunger 5 by rotating plunger 5 with respect to barrel 10 as shown in FIGS. 3, 6, and 7. Handle 19 may be attached to and rotate with plunger 5, or handle 19 may be rotatably attached to barrel 10 wherein threaded plunger 5 is inserted into a aperture of handle 19 and plunger 5 may be advanced or retracted within barrel 10 by rotating handle 19. In this embodiment, the rotation of barrel 10 may be restricted by the operator or by any other suitable means, including, but no limited to a clamp or another operator, and the rotation of plunger 5 may be restricted by a pin or guide disposed on plunger 5, preferably at or near the distal end of plunger 5 that slidably engages a channel in barrel 10 that restricts the rotation of plunger 5, with respect to barrel 10. In one embodiment advancement mechanism 7 may be a ratchet mechanism, such as, but not limited to, a caulking gun-type ratchet mechanism that may be used to advance and/or withdraw plunger 5 as shown in FIG. 4. Advancement mechanism 7 may also be motorized to allow a more remote, and/or controllable, delivery, for radiation protection of operator and staff.

Thermal jacket 8 may have first and second end walls and either one external wall, or one external wall and one internal wall. First and second end walls are connected by the one external wall or the one external wall and the one internal wall. Thermal jacket 8 surrounds at least a portion of the length of barrel 10 creating thermal space 11 either between jacket 8 and barrel 10, or if jacket 8 comprises an internal wall, thermal space 11 is created between the internal and external wall of jacket 8. In one embodiment thermal jacket 8 comprises a first end wall, a second end wall, and an external wall connecting the first and second end wall to form a tubular structure. Jacket 8 may possibly extend down over distal segment 4 as well as shown in FIGS. 2, 3, and 5. In one embodiment jacket 8 is a barrel-like structure comprising an exterior wall that may be cylindrical in shape having a two end walls, one disposed on, and connected to, each end of the cylinder. Although a cylinder shape is shown, the jacket may be any other suitable shape, including, but not limited to, a square, rectangle, triangle, or polygon. An opening may be formed in both end walls to allow insertion of barrel 10. The opening is sized to fit snugly around the outer wall of barrel 10. In one embodiment a gasket, or a series of multiple-sized gaskets, may be used to form a snug fit around barrel 10 (not shown). In one embodiment jacket 8 may be permanently attached to barrel 10, or one end wall of jacket 8 may be permanently attached to barrel 10 and the other end may be movable about the length of barrel 10 wherein jacket 8 comprises at least two sections collapsible into one another.

Heating and cooling or isothermal elements may be placed within thermal in or around space 11. This could include warm or cool liquids or gels, for instance, but not limited to, water and/or saline, chemical agents for heating or cooling reactions or an electrical element 18 for warming. Room temperature liquid, such as saline, could be used for isothermal consistency between one procedure and another. Jacket 8 could also have cooling and heating segments in sequence to alter the cement polymerization reaction accordingly, for example, to slow and then accelerate polymerization or vice versa.

At least one port 9 may disposed on jacket 8 and in communication with thermal space 11. Port 9 may have a Luer-lock type connector that allows introduction of thermal material such as saline, or any other suitable material. In one embodiment, two ports 9 are disposed on jacket 8 and are in communication with space 11. This allows for easier introduction of thermal material, and also permits the circulation of thermal material within space 11 of jacket 8. Port 9 may also be capped on both ends to allow a closed system or can be connected to tubing for circulating liquid of a desired temperature.

Proximal end 13 of injector barrel 10 may have a Luer lock type connector for introducing liquid cement into injector barrel 10. In an embodiment, the length of thermal jacket 8 along injector barrel 10 may be about 60 cm and to hold about 4.5 cc of cement with a diameter similar to at least one commercially available cement injectors. This could vary depending on the size of the injector barrel and desired surface area of the injector for thermal exchange.

In an embodiment, injector barrel 10 is a narrow barrel syringe (similar in size to the vertebroplasty or kyphoplasty cannula) to provide a mechanical advantage. Injection may require an elongated barrel 10 to contain the necessary cement volume, and this also helps increase the distance of the operator from the radiation source. Another beneficial effect is increased surface area for heat exchange with thermal jacket 8. The elongated injector barrel 10 may require a flexible approximately 90 degree turn or bend capability to allow positioning an x-ray image intensifier closer to the patient, and this helps reduce radiation exposure. The thin elongated injector barrel 10 may be a rigid metal, plastic, or synthetic tubing but having a distal flexible segment 4 allowing a 90 degree bend to connect with needle 2. In an embodiment injector barrel 10 may be flexible throughout but made of non-compliant material. Needle 2 may be, but is not limited to, a vertebroplasty or kyphoplasty needle. Plunger 5 for barrel 10 may be flexible or partly rigid.

In an embodiment plunger 5 may be straight and elongated or may be flexible and allow for mechanism 7 to be a more compact ratchet-type injector with plunger 5 rolled into a coil and advanced with the ratcheting mechanism, as shown in FIG. 4. In an embodiment, plunger 5 or mechanism 7 may be motor-driven. This would allow for remote control of unit and decreased radiation exposure during cement delivery. Temperature feedback employing a thermocouple could be used to modify the delivery rate for the cement. The percutaneous cannula attached to the thin syringe barrel may be attached directly or attached to the syringe and then introduced to the patient with a co-axial guide cannula.

In an embodiment thermal jacket 8 has an elongated surface area along the thin injector syringe barrel 10. Jacket 8 may be attached or removable. Removable jacket 8 is shown in FIG. 7. Jacket 8 may be used with other injectors and larger syringes or mixing chambers. With small thin injector barrels 10, multiple injectors could be placed in one thermal source. The temperature in jacket 8 may be modified by heating it with warm liquid such as water or saline or with chemical reactions. Jacket 8 could be warmed in whole or part by electrical (battery or other powered) source. The warm solution can be administered continuously through an IV line setup, a pump, pushed intermittently from a large syringe, from a water tap, or by any other suitable means. Jacket 8 may be a closed system containing a thermal material that may be pre-cooled or pre-heated. Temperature control may be continuous or variable or sequential (hot/cold) along the length of the injector. Variable temperature control may be programmed to respond to temperature or viscosity feedback from the cement at the tip, or at any point along the length, of the injector. Electronical resistor (heating) element 18 may be built directly into barrel 10 wall, jacket 8 wall, or both. Radio frequency may also be used. This could also facilitate continuous monitoring of cement volume delivered. In an embodiment an injector syringe with at least two barrels 10 could be filled to allow delivery of warmed or cooled cement alternatively.

In an embodiment the invention may comprise an elongated syringe, which may be, but is not necessarily, similar in caliber to the size of the vertebroplasty needle for mechanical advantage, or may be narrower in caliber than a typical syringe. A portion of the injector barrel 10 may bend to approximately 90 degrees to help distance the operator from the x-ray beam and have a shorter object to image intensifier distance for radiation safety. The invention comprises thermal jacket 8 around all or part of injector barrel 10 for temperature control of the cement polymerization reaction, and the small caliber syringe barrel 10 also has greater surface area for heat exchange with thermal jacket 8.

In an embodiment injector barrel 10 may be used without thermal jacket 8 and/or thermal jacket 8 may be used with other injectors or tubing for cement delivery. In an embodiment injector barrel 10 may be made of flexible material throughout its length. In an embodiment thermal jacket 8 may be used on other types of injector barrels or mixing chambers. In an embodiment thermal jacket 8 may be a simple sleeve or an array of sleeves that contain a warm or cool fluid or element (including electrical). In an embodiment thermal jacket may have more than one temperature element in series for cooling and warming.

One embodiment comprises a dual chamber injector sharing a common thermal jacket to ensure the same temperature in two injectors being used simultaneously to treat a single vertebra through two needles. For example, dual injector barrels 10 may be useful for the motor driven system to keep both devices 100 pushing the same viscosity of cement, for a simultaneous dual needle injection system.

In one embodiment, thermal jacket 8 may be disposed in or around the initial mixing chamber for the bone cement. Therefore the mixed components would be at a desired warm or cool temperature before delivery to the thermally controlled injector. In one embodiment the injector may have a reservoir chamber with a cool thermal jacket, and the desired quantity of bone cement could be injected into a second chamber for warming and use. The remainder of the bone cement in the cooled reservoir could be used later in the same procedure or to treat a second vertebra.

Figures 5A, 5B:
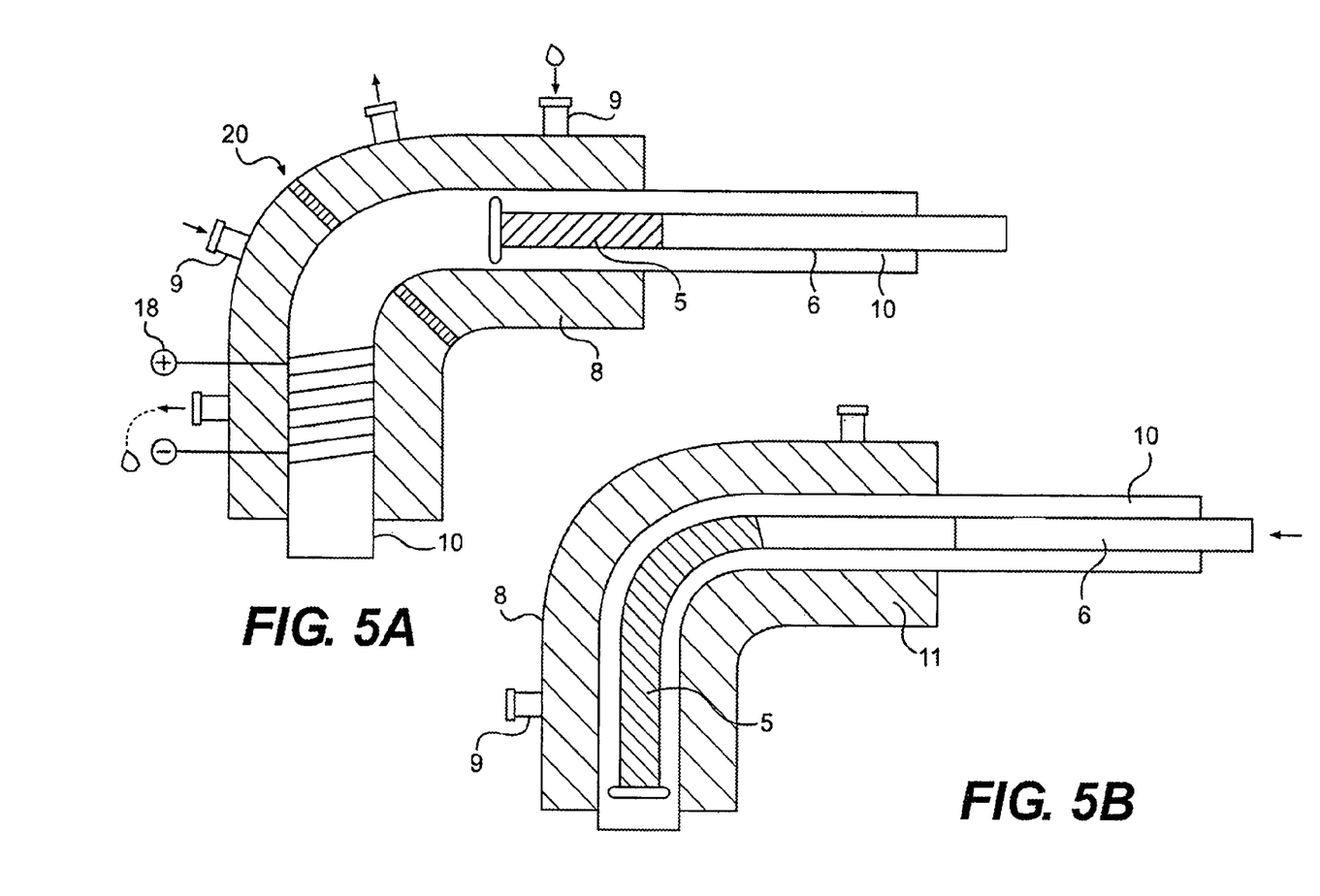
FIG. 5 is a cross-section detail view of an embodiment of the present invention including a thermal jacket and a heating element.

FIGS. 5A and 5B show flexible plunger 5, two serial thermal jackets 8, or in the alternative, one thermal jacket 8 with partition 20 to permit the use of two chambers of different temperatures, and heater element 18. A thermocouple could also be included with or incorporated near the heater element to measure and display the cement temperature as it is being delivered, and in one embodiment, feedback to a computer control. Sensors for injection pressure and volume may also be added.

As shown in FIG. 6, in one embodiment plunger 5 and barrel 10 may assume different shapes other than the elongated tubular structure. The shapes, including, but not limited to, may be triangular, square, rectangular, cross, or star shapes, serve to increase the surface area for thermal exchange between injector barrel 10 and thermal jacket 8. One is a rectangular shaped barrel on cross section and the other is in the shape of a "plus" sign on cross section. Triangular shapes or other versions could also have advantages. The exterior wall of thermal jacket 8 may remain round in shape. FIG. 6 also shows Handle 19 with a threaded plunger 5 that may be lengthened to provide additional distance between the operator and the source of the radiation, for example, an x-ray beam.

FIG. 7 shows thermal jacket 8 which may be adaptable to other commercially available injectors and is removable to allow changing from a cool temperature jacket to a warm jacket by manual exchange.

Thermal jacket 8 may have an opening 23 along its length to allow jacket 8 to be positioned around barrel 10. Jacket 8 may be comprised of a material flexible enough to permit insertion of barrel 10 though the longitudinal opening, or jacket 8 may comprise hinge 21 to allow the opening of jacket 8. Hinge 21 may be comprised of a flexible material that permits the flow of the thermal element through hinge 21, or may be a hinge comprised of any suitable material, such as, but not limited to, metal or plastic, wherein tube 22 may be needed to aid in the circulation of the thermal element within jacket 8.

Example

Jacket 8 was initially filled with iced water to keep the cement useable, and when ready for use the ice water was replaced by hot water from a standard water tap to start the polymerization reaction. The cooled jacket 8 kept the cement liquid for approximately 30 minutes (longer than usual set time) and approximately 2 minutes after hot water was infused into jacket 8 the cement was ready to inject and was usable for approximately 3.5 minutes. This device and method allows the operator to have the cement prepared ahead of time and to be ready "on demand." In one embodiment the operator may freeze the jacket filled with saline or water and then replace the cooled jacket with a warm jacket when ready to use. In this example, the use of thermal jacket 8 utilizes the thermal properties of the polymerization reaction of PMMA (polymethylmethacrylate) to help control the delivery of the bone cement and make it more consistent regardless of room temperature or other temperature variables. The low compliance system with the elongated barrel injector also incorporates 1) length to get distance from the radiation field and 2) by using one injector per needle, with no exchanges, decrease the need for the operator to move back and forth to inject or re-attach the injector to the needle. For example, device 100 may also be used for sacroplasty of the sacrum, acetabuloplasty of the acetabulum or various other osteoplasties such as areas of fracture, particularly as caused by cancer or trauma. Other bone filler materials could be injected such as bone morphogenic protein.

It will be apparent to those skilled in the art that variations and modifications of the present invention can be made without departing from the scope or spirit of the invention. Thus, it is intended that the present invention cover all such modifications and variations of the invention, provided they come within the scope of the appended claims and their equivalents.

I claim:

1. An apparatus for injecting a material comprising:
an injector barrel in communication with a delivery needle and a plunger,
wherein at least a portion of the plunger is slidably disposed within a proximal portion of the injector barrel, and a proximal end of the delivery needle is in communication with a distal end of the injector barrel,
a thermal jacket surrounding at least a portion of the length of the injector barrel, wherein the thermal jacket comprises an interior wall, an exterior wall, and first and second end walls connected to the interior and exterior walls creating a closed tubular system enclosing a thermal space;
wherein the thermal jacket comprises a port disposed on the exterior wall and in communication with the thermal space.

2. The apparatus according to claim 1, comprising an introducer cannula.

3. The apparatus according to claim 1, wherein the injector barrel incorporates a flexible distal segment near the distal end of the injector barrel.

4. The apparatus according to claim 1, wherein a distal portion of the plunger is flexible.

5. The apparatus according to claim 1, comprising an advancement mechanism in communication with the plunger.

6. The apparatus according to claim 1, comprising a heating element disposed on the injector barrel.

7. An apparatus for injecting a material, comprising:
an injector barrel with a proximal and a distal end, wherein the distal end is in communication with a delivery needle;
a plunger with a proximal end and a distal end, wherein a portion of the distal end is in communication with the proximal end of the injector barrel, wherein at least a portion of the plunger is slidably disposed within the injector barrel; and
a thermal jacket surrounding at least a portion of the length of the injector barrel, wherein the thermal jacket comprises an interior wall and exterior wall joined by a first end wall and a second end wall, wherein the thermal jacket comprises at least two chambers with a partition to isolate the two chambers from one another.

8. The apparatus according to claim 7 wherein the thermal jacket comprises a port disposed on the exterior wall and in communication with a thermal space created by the exterior wall, interior wall, and first and second end walls.

9. The apparatus according to claim 7, wherein a heating element is disposed on the thermal jacket.

10. The apparatus according to claim 9 wherein the heating element is disposed at the distal end of the thermal jacket.

11. The apparatus according to claim 7 wherein the thermal jacket has an opening along its length.

12. The apparatus according to claim 11, wherein the thermal jacket has a hinge disposed on the external wall opposite the opening.

13. An apparatus for injecting a material comprising:
an injector barrel;
a plunger;
a thermal jacket, wherein the thermal jacket contains both a cooling portion and a heating portion.

14. The apparatus according to claim 13 wherein the cooling portion is
cooled by the circulation of a cold liquid in the thermal jacket.

15. The apparatus according to claim 13 wherein the heating portion is
an electric coil.

16. An apparatus for injecting a material comprising:
an injector barrel in communication with a delivery needle and a plunger, wherein at least a portion of the plunger is slidably disposed within a proximal portion of the injector barrel, and a proximal end of the delivery needle is in communication with a distal end of the injector barrel,
a thermal jacket surrounding at least a portion of the length of the injector barrel, wherein the thermal jacket comprises an interior wall, an exterior wall, and first and second end walls connected to the interior and exterior walls creating a closed tubular system enclosing a thermal space,
wherein the thermal jacket has an opening along its length, and
wherein the thermal jacket has a hinge disposed on the external wall opposite the opening.

17. The apparatus according to claim 16 wherein the thermal jacket surrounds at least a portion of the length of at least two injector barrels.

* * * * *